United States Patent [19]
Bodó et al.

[11] Patent Number: 5,584,297
[45] Date of Patent: Dec. 17, 1996

[54] PROCESS AND EQUIPMENT FOR DIAGNOSING CIRCULATION (CEREBROVASCULAR) DISORDERS

[75] Inventors: Mihály Bodó; István Nagy; János Peredi; György Thuróczy; László Ozsvald, all of Budapest, Hungary

[73] Assignee: LRT, Inc., Chicago, Ill.

[21] Appl. No.: 313,218

[22] PCT Filed: Feb. 8, 1993

[86] PCT No.: PCT/HU93/00006

§ 371 Date: Nov. 28, 1994

§ 102(e) Date: Nov. 28, 1994

[87] PCT Pub. No.: WO93/19665

PCT Pub. Date: Oct. 14, 1993

[30] Foreign Application Priority Data

Mar. 31, 1992 [HU] Hungary ............... P 92 01079

[51] Int. Cl.$^6$ ........................... A61B 5/02
[52] U.S. Cl. ............... 128/670; 128/700; 128/668
[58] Field of Search .................... 128/630, 666, 128/667, 668, 669, 670, 671, 672, 700

[56] References Cited

U.S. PATENT DOCUMENTS

| | | | |
|---|---|---|---|
| 4,137,908 | 2/1979 | Degonde et al. | 128/700 |
| 4,860,759 | 8/1989 | Kahn et al. | 128/668 |
| 5,025,784 | 6/1991 | Shao et al. | 128/700 |
| 5,108,363 | 4/1992 | Tuttle et al. | 128/668 |
| 5,343,867 | 9/1994 | Shankur | 128/668 |
| 5,379,774 | 1/1995 | Nishimura et al. | 128/667 |

FOREIGN PATENT DOCUMENTS

| | | | |
|---|---|---|---|
| 0212278 | 3/1987 | European Pat. Off. | A61B 5/02 |
| 3807672 | 9/1989 | Germany | A61B 5/02 |

Primary Examiner—Angela D. Sykes
Assistant Examiner—Stephen Huane
Attorney, Agent, or Firm—Oliff & Berridge

[57] ABSTRACT

A method and apparatus diagnose a circulation disorder in a patient, and in particular, predict whether a patient is likely to suffer a stroke. The diagnosis is made based on a patient's responses to questions regarding whether the patient has experienced symptoms of a neurological disorder, and based on sensed electrical brain activity and sensed blood pulse activity. The pulse measurements may be taken at the patient's head, and/or at the patient's arms and/or legs. The diagnosis may be based upon a comparison of the patient's electrical brain activity on the right and left sides of the patient's brain, and on a comparison of the pulse activity on the right and left sides of the patient's head, arms and legs. The diagnosis may also be based on the patient's electrical heart activity. The diagnosis may further be based on the results of a stress test that measures the patient's blood pressure, pulse rate and anxiety level. Such a stress test may be performed before and/or after the patient's electrical brain activity, blood pulse activity and electrical heart activity have been measured. The diagnosis may also be based on whether the patient exhibits one or more arteriosclerosis risk factors and based on patient data such as age, weight, height, sex, blood cholesterol level and blood sugar level.

26 Claims, 4 Drawing Sheets

5,584,297

PROCESS AND EQUIPMENT FOR DIAGNOSING CIRCULATION (CEREBROVASCULAR) DISORDERS

BACKGROUND OF THE INVENTION

The invention relates to a process for diagnosing circulation (cerebrovascular) disorders, in order to recognize vascular diseases at the possible earliest time and makes the screening of cerebrovascular affectedness and threatenedness possible. The invention relates also to the equipment for effectuating the process.

Among the cases of death, the diseases of heart, circulation and vascular system take worldwide a leading place. Thus, their healing has a prominent importance and the medicine makes strong efforts for the improvement of treatment and effective prevention. The precondition of an efficient healing and well-timed intervention is the comprehensive and good diagnostic work.

According to the present practice of medical diagnostics various electrodiagnostical examinations are successively carried out for exploration of cerebrovascular disorders on the basis of complaints of the patient. Such examinations are e.g.: ECG (electrocardiography), EEG (electroencephalography) as well as the measurement of pulse wave. From the analogue signals obtained from these examinations, the neurologist physician states a diagnosis or affords an information of diagnostical value.

On examination of the vascular system diseases diagnostical curves are taken up (plotted), usually by the means of an instrument working on the basis of Doppler effect.

The greatest drawback of the present investigating methods is that the separate examinations are carried out separately in space and in time usually by not the same neurologist, physician since internists, cardiologists, specialists of the heart and vascular system, angiologists and the like work separately and the data taken up successively—and not simultaneously—do not provide an information of satisfying accuracy from the status of the person examined. The data recorded in time points differing from another do not permit to obtain finer, more graded information, which can be concluded from connections between the separated parameters; or to accomplish the most effective preventive and complex measures to be done on the basis thereof. Of course, the present methods of examination have also the drawback that the patient has to visit the various diagnostic sections (departments) for the informations needed to the differential diagnostics which can be received in several cases only in a troublesome and complicated manner. A further disadvantage of the present diagnostical examination methods is that they (including the Doppler effect) are unuseful to state (detect) the arteriosclerosis in its quite advanced phase.

SUMMARY OF THE INVENTION

The task of the invention is to provide a process for diagnosing disorders, in other words: for establishing (ascertaining) human arteriosclerosis, which process makes possible to recognize the circulation system of the person examined in a complex and highest fineness (in the fullest detail) in a simple manner, within a short time; and which, thereby affords the possibility to select not only the best (optimum) method(s) or treatment of healing, respectively but also to intervene prophylactically e.g. in the processes of sclerosis so early that it has not been possible by the examination-diagnostic methods known at present. A further task of the invention is to provide a modern equipment for accomplishing (effectuating) the process.

The invention is based on the following recognitions. From the viewpoint of examination of the status of whole circulation system, the investigation of cerebral blood flow and within this, the investigation of decrease in the function of cerebral vessels bears a prominent importance. This function decrease may be caused by an illness or aging and can quantitatively be stated. An other one of our recognitions is that it is indispensable to weigh also the peripheral circulation and phychophysiological status together with determination of the cerebrovascular orientation to assure a complex result with a highest fineness. Furthermore, it has been recognized that the precondition for an optimum diagnosis is the combined use of filling out an informative (information) questionary (interrogating of the person examined) and instrumental examination. Based on the informations arising from these sources of two kinds, a diagnosis can be established, which is more accurate and fine than any of the earlier ones and provides the possibility of an early prophylactic intervention, too.

Based on the above recognitions, the set task has been solved according to the invention by the means of a process, in the course of which arterial blood flow parameters are measured and recorded, and a diagnosis is stated on the basis of the results obtained. It is characteristic of this process that:

a) questions are posed to the patient in relation to his neurological status and the responses are recorded;

b) the brain electrical activity, rheographic pulse waves on the head and extremities and electrical activity of the heart of the patient are instrumentally measured and recorded;

c) the data of verbal and instrumental examinations are evaluated together and the diagnosis is established on the basis of this common evaluation. By the means of this process the subjective and objective data of human arteriosclerosis can be collected and (numerically) measured partly by weighing the neurological symptoms indicating a disturbance in the brain circulation, and partly by informations containing the accentuated risk factors /stress, smoking, elevated (high) blood pressure, diabetes, heart disease, alcohol consumption and the like/, too. In the process, the measurement and data processing of the physiological parameters occur parallelly or substantially parallelly during a short period. In the course of this, in addition to the traditional (conservative) processings, an important viewpoint is to clear up the relations (connections) and informations between the separate (individual) parameters and to draw a diagnostical conclusion therefrom (e.g. ECG+pulse wave=pulse delay) as well as to perform simultaneous measurements practically extended to the whole body (head, hands, feet) in at least three modalities. These latter ones are EEG, rheogram and rheoencephalogram parallelly with ECG.

The process provides simultaneous examination of data and physiological indices accomplishing a data processing of novel conception, which is not common in the present medical practice. This is achieved by using the GRAL language, which can be described by the principle of intermodal information treatment and mathematically approximated through the time series analysis.

Within the complexity mentioned above, the system pronouncedly builds on the measurement of the pathological phenomenon called as decrease in the wind box function of the vessel wall, which means the decrease in the elasticity of vascular wall because of aging or arteriosclerosis, respectively.

On the basis of these, the process is useful for the numerical measurement (quantitative measurement) of deterioration (disease) occurring in the status of circulation of the brain and extremities; detecting and following it in the earliest phase; large-scale (mass) screening examinations; following the drug action; intensive patient-monitoring as well as visualisation and archivation of the recorded physiological indices (parameters) in the form of analogue curves. It is suitable to solve tasks of preparing decisions (diagnostics) and to be transformed to an expert system in the case of built in limit establishments.

According to a preferred way of implementation of the process, the verbal and instrumental examinations are successively carried out one after each other. According to an other criterion of the process, first the major part of verbal examination, then the instrumental examination and subsequently, the remaining part of the verbal examination are carried out; it is suitable to perform in the first verbal examination a first stress examination comprising (including) the measurement of blood pressure and heart rate (pulse frequency) in order to establish the vegetative balance and to perform a similar second stress examination in the residual part of the verbal examination.

According to an other preferred way of implementation of the process, the risk factors of arteriosclerosis, in particular smoke, systematic alcohol consumption, diabetes, heart disease and high blood pressure are stated in the verbal examination.

The equipment serving for the implementation of the process includes a computer. It is characteristic of this equipment that the computer is connected through a data-transfer channel with a patient-inserting unit containing signal receiver-transformer channels for recording and transfer of human physiological parameters, data-collecting unit and supply unit; whereas the computer contains an inserting card relating to the patient. The data are stored in a magic database-treating system; the analogue signal processing is realized by the means of the GRAL programme and displayed by own developed visualizing program (Redirec). The operation suitably occurs by using a patient-inserting unit conveniently connected before the IBM-compatible AT computer, which unit contains therefore the analogue measuring unit (receiving, amplifying and coding the physiological signals of the patient), the measurement data-collecting (processing) unit as well as the supply unit (corresponding to the IEC 601 standard) providing the operation thereof. The computer contains the inserting card of the patient.

In the following, the invention is described on the basis of the enclosed drawings, which contain the devices useful for implementation of the invention as well as illustrate block schemes and results of determinations. In the drawings:

DETAILED DESCRIPTION OF PREFERRED EMBODIMENTS

Figure 1:
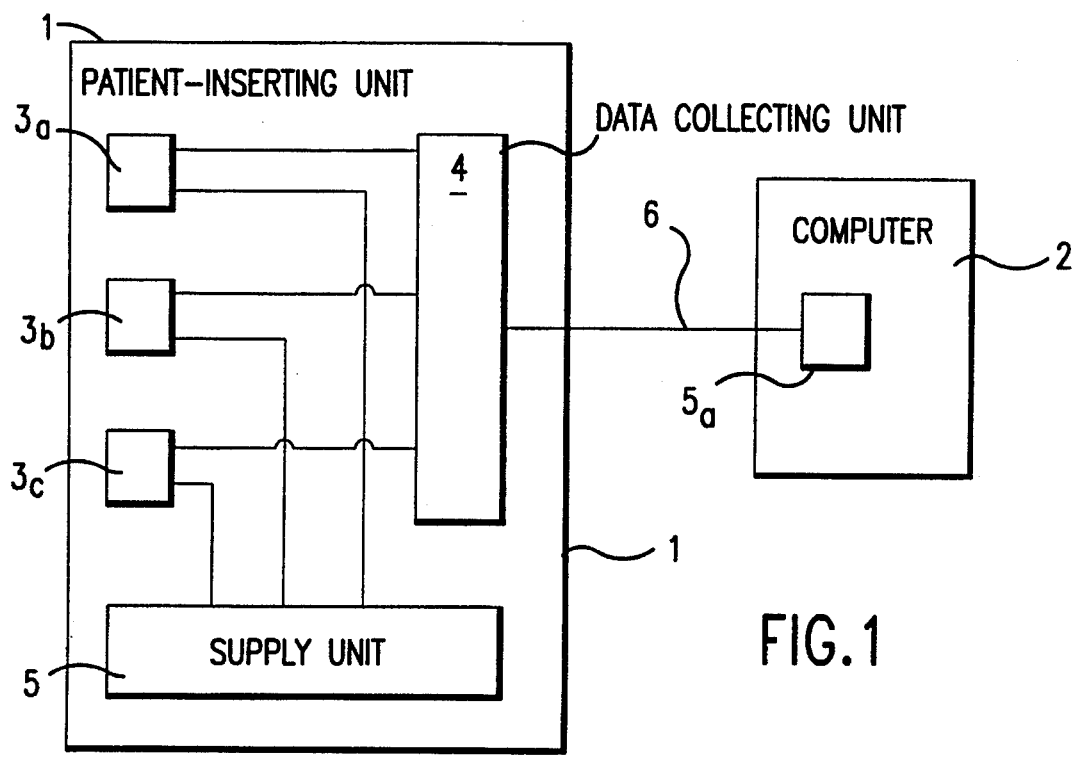
FIG. 1 is a schematic block diagram of a preferred example of the equipment useful for the process.

Computer 2 (which may be e.g. an IBM-AT computer) of the equipment visible in FIG. 1 is connected through the data transfer channel 6 with the patient-inserting unit signed by reference number 1 as a whole. This latter one possesses the signal receiver-transformer channels 3a–3c, data-collecting unit 4, supply unit 5 and inserting card 5a. The signal receiver-transformer channels 3a–3c serve for receiving, amplifying and transmission of the physiological signals of the patient. The data-collecting unit 4 transmits the measurement results. Computer 2 stores and evaluates the measurement results and informations obtained by interrogating. The supply unit 5 connected with the signal receiver-transformer channels 3a–3c is preferably a type corresponding to the prescriptions of IEC-601. The data transfer channel 6 is a highspeed, galvanic separated two-way data transfer channel.

Figure 2:
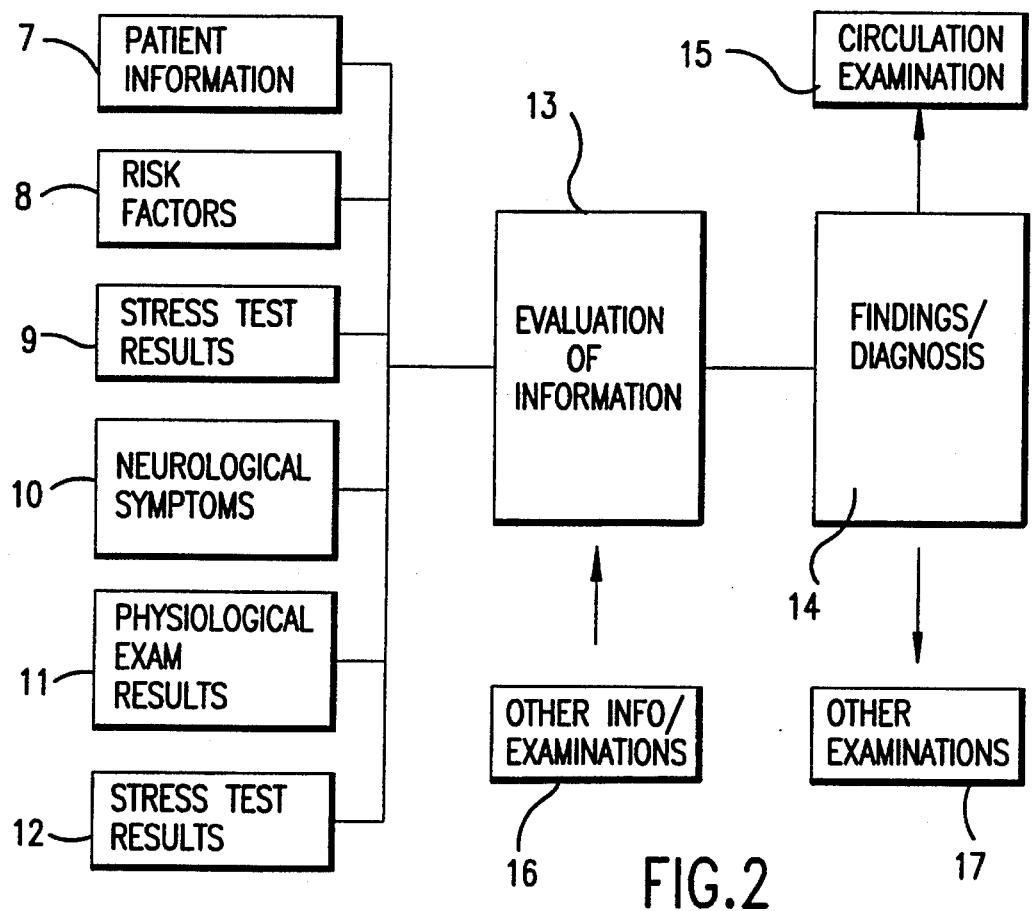
FIG. 2 is a block diagram of an examination process according to the invention.

In FIG. 2, the individual blocks represent the most important phases of examination, i.e. of the process according to the invention. Block 7 contains the identifying questions and responses directed to the subject of the patient (name, data of birth, sex, body weight, height, time Of examination and the like). The questions and responses relating to the common diseases and risk factors (smoking, systematic consumption of alcohol, elevated blood pressure, heart disease, diabetes) are incorporated to block 8.

The result of the first verbal stress examination (investigation of the psychophysiological status) supplemented with blood pressure and heart rate measurements arrive at block 9. In the case of an examination by questionary, the respective part of questionary is assembled as follows.

TABLE 1

| PSYCHOPHYSIOLOGICAL STATUS (at the start of examination - "just now") | |
|---|---|
| Blood pressure | Hgmm Heart rate /min |
| I feel myself to be care-free | (1,2,3,4) |
| I am nervous | (1,2,3,4) |
| I am free of any tension | (1,2,3,4) |
| I am satisfied | (1,2,3,4) |
| I am anxious | (1,2,3,4) |

1 = not at all;
2 = in some measure;
3 = fairly;
4 = very/fully

Neurological questions and responses (related to cerebrovascular spasms; TIA/Transient Ischemic attack/)belong to block 10, which can be included to a questionary e.g. in the manner according to Table 2.

TABLE 2

| Sign it by X when any of the complaints listed has earlier occurred | | | |
|---|---|---|---|
| Neurology I. | | | |
| Temporary weakness | | | |
| on one extremity | ... X | on extremities of one side | ... X |
| on all the four | ... X | on more extremities or in | ... X |

TABLE 2-continued

Sign it by X when any of the complaints listed has earlier occurred extremities                other form
Temporary numbness, sensory decrease or defect

| | | | |
|---|---|---|---|
| on one extremity | ... X | on extremities of one side | ... X |
| on all the four extremities | ... X | on more extremities or in other form | ... X |
| on the face or trunk | ... X | | |

Temporary disturbance in the speaking (difficulty in the Phonetics and apperception of words)
Temporary disturbance in the vision

| | |
|---|---|
| temporary disturbance or defect of vision of one eye | ... X |
| disturbances in the vision of both eyes    ... X   Diplopia | ... X |

Neurology II.

Temporary dysphagia

Dizziness
| | |
|---|---|
| rotary vertigo | ... X |
| feeling of uncertainty (decisively in one direction, e.g. to the left) | ... X |
| feeling of uncertainty (without directedness) | ... X |
| Temporary apraxia of one extremity or extremities | ... X |
| Loss of memory or temporary defect of memory | ... X |
| Temporary disturbance of reading, writing, counting or spatial orientation | ... X |
| Did you have any temporary disturbance being of neurological origin in your opinion | ... X |

Block 11 is the block of physiological examinations. Within the framework of physiological examinations: the brain electric activity (EEG, i.e. electroencephalogram) is measured through the signal receiver-transformer channels 3a–3c visible in FIG. 1; electric heart examination (ECG, i.e. electrocardiogram) is carried out; and the pulses both on the head (REG, i.e. rheoncephalogram) as well as on the extremities (rheographic or impedance pulse) are recorded. The measurement data recorded are summarized in a table (see later).

Block 12 corresponds to a second stress examination (investigation of the psychophysiological status), which is carried out precisely according to the first such examination (Table 1).

Block 13 relates to the evaluation summarizing the result of verbal and instrumental examination as described above and supplementing those with the results of other examination(s) (absent from the questionary) arising from block 16; such other examinations are chiefly directed to the determination of blood cholesterol and blood sugar level as well as they comprise an ophthalmologic (fundus) examination.

Block 14 represents the findings, i.e. the guiding diagnosis, which can be assembled as a part of a questionary according to the following Table 3.

TABLE 3

Opinion
(sign the opinion selected by X)

| | | |
|---|---|---|
| 1. | Neither cerebral circulation disturbance nor data indicating it are present | ... X |
| 2. | The uncertainty of complaints and/or findings further on require control (medical observation) | ... X |
| 3. | Check-up is suggested because of suspicion of cerebral circulation disturbance | ... X |
| 4. | Check-up is suggested because of suspicion of peripheral circulation disturbance | ... X |

TABLE 3-continued

Opinion
(sign the opinion selected by X)

| | | |
|---|---|---|
| 5. | Internal or neurological check-up is suggested | ... X |

Based on the findings, i.e. diagnosis, the physician may propose the patient to carry out additional examination. Block 15 represents the carrying out of blood circulation examination (Doppler control) whereas block 17 corresponds to other examinations possibly required on the basis of findings (block 14).

Figure 3:
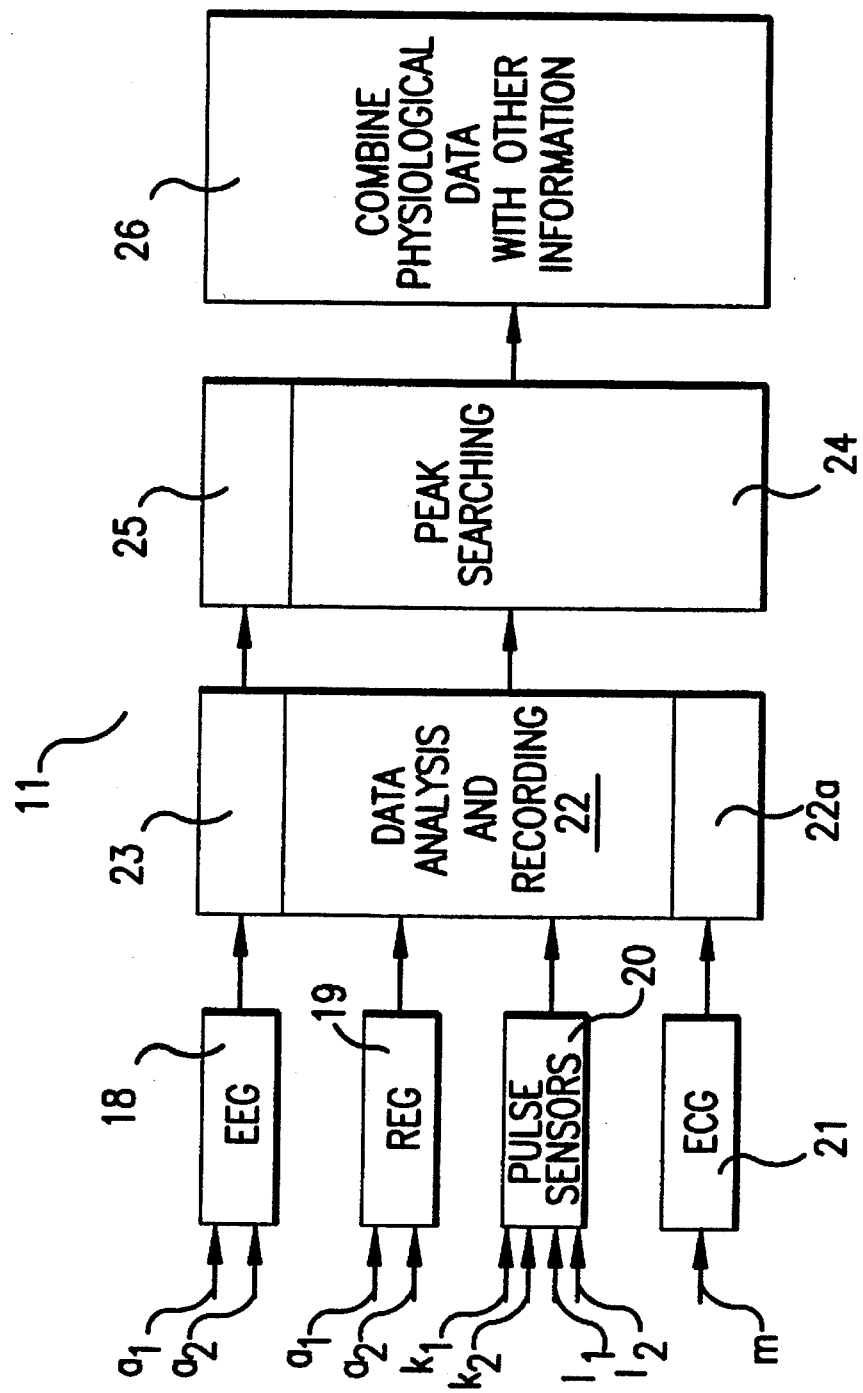
FIG. 3 is a conceptual drawing of measurement and data processing of physiological functions of a patient.

In FIG. 3, the block 11 indicated in FIG. 2 relating to the instrumental physiological examination is illustrated in detail. FIG. 3 actually demonstrates a process organization. Block 18 is the block of EEG (electroencephalogram examination and instrument): the arrow $a_1$ corresponds to the informations obtained from the right side of head whereas arrow $a_2$ indicates the informations measured on the left side of head. Block 19 represents the REG (rheoencephalogram) examination the meanings of arrows $a_1$ and $a_2$ are the same as given for the block 18.

Block 20 relates to the instrumental examination (measurement) of the pulse (heart rate); arrows $k_1$ and $k_2$ show the pulse signals of the right or left hand, respectively, whereas arrows $l_1$ and $l_2$ demonstrate the pulse signals taken from the right or left foot, respectively. Block 21 is the block of ECG lead II; and the arrow m shows the data transfer channel. The signal receive-transformer channels 3a–3c of the equipment according to FIG. 1 are provided for carrying out the operations corresponding to blocks 18–21.

Block 23 corresponds to a computer related activity, to a rapid Fourier analysis known in se; whereas block 22 represents a computer-aided averaging separately occurring in each case. An averaging operation takes place during about 40 seconds. Block 22a is needed to the procedures demonstrated by blocks 22 and 23 for computer-related reasons: it demonstrates the formation of the trigger pulse arising from the ECG signal (the reference signal is the "R" wave of ECG).

Block 24 is the block of peak-search; block 25 is that of EEG-related spectrum peak-search; these are maximum-minimum searching calculating operations.

Finally, block 26 corresponds to a part of questionary, wherein the calculated values of instrumental examination (blocks 24 and 25) are inscribed to the questionary (see Table 4 later) The values arriving at the block 26 are usually computer-calculated asymmetry values, the values obtained from the right-side body parts are considered as basal values and values calculated from the left side are formed in relation to these.

Figure 4:
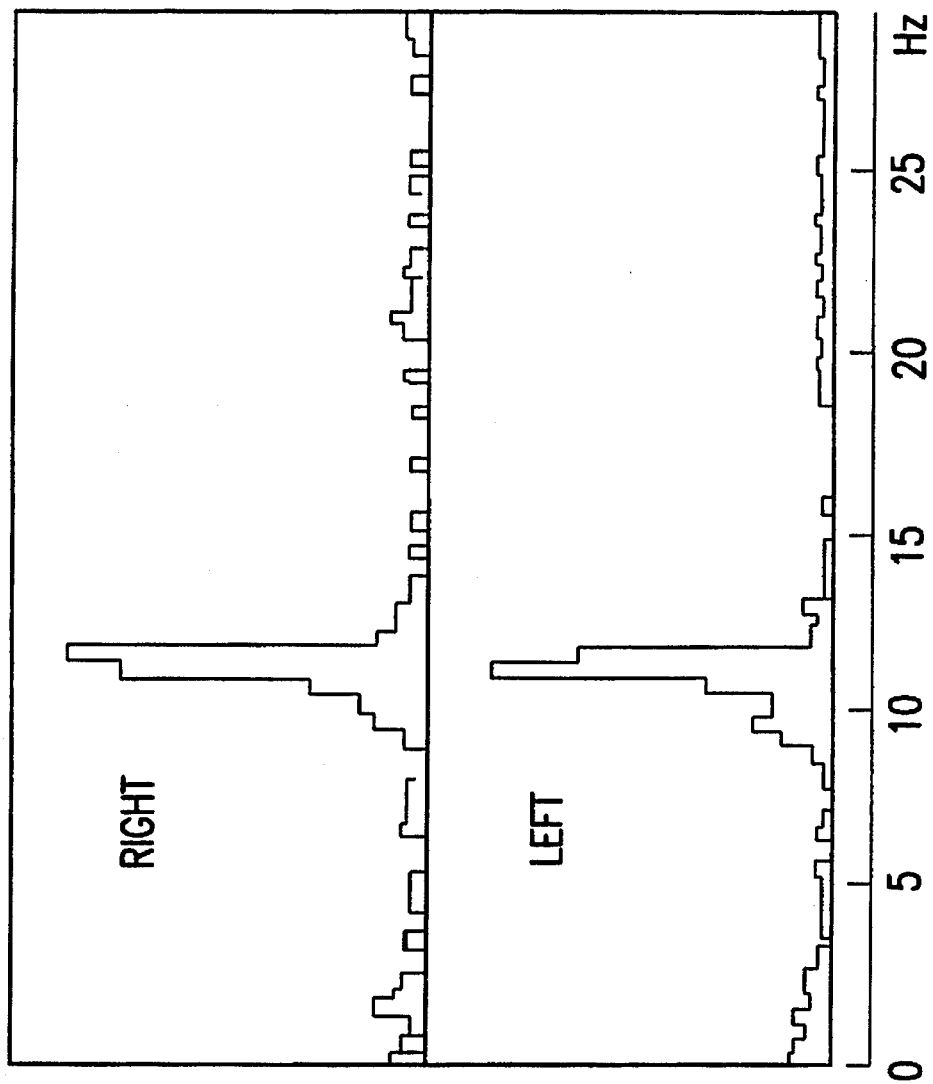
FIG. 4 shows a graphical representation of results of a frequency analysis (EEG examination) carried out on the right and left side of head of a patient.

In FIG. 4, the graphically illustrated final result of procedures described in relation to blocks 18, 23 and 25 according to FIG. 3, can be seen, i.e. the Figure is the representation of the examination of EEG spectrum of both brain hemispheres in a specific case. The results of instrumental measurements obtained from the left hemisphere are visible below, those obtained from the right hemisphere can be seen above, which are the average of about 40 measurement values. FIG. 4 proves that, in the given specific case, no difference exists between the electric activity (background) of the right and left brain hemispheres of the patient. It should be noted that, according to the worldwide accepted standpoint, a difference of about 30% in the EEG amplitudes is not pathologic but allowed in the practice.

In the case according to FIG. 4, the percentage difference between the two brain hemispheres is negligible since this is not a "native" curve but it can be considered to be magnified several hundred times since it was prepared by the computer.

Figure 5:
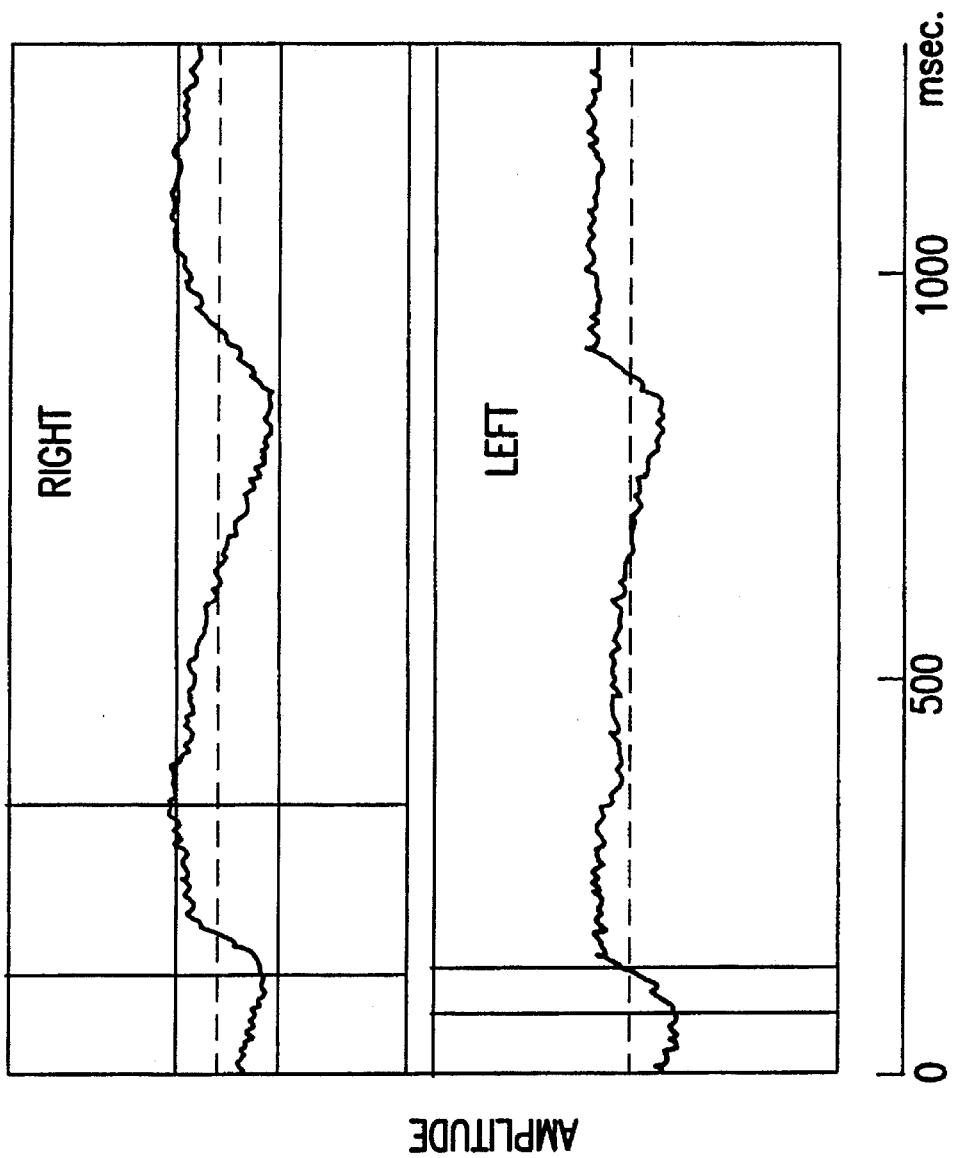
FIG. 5 is a graphical representation of results of pulse wave measurements carried out on the right side and left side of the head of a patient.

In FIG. 5, the graphically illustrated final results of procedures described in relation to blocks 19, 22 and 24 according to FIG. 3 can be seen: the pulse waves (REG examination) arising from the right and left brain hemispheres of the same patient are shown whom FIG. 4 relates to. Also in this case, the pulse wave starting from the left brain hemisphere is illustrated below, that starting from the right hemisphere is shown above (average of about 40 measurements). It appears unequivocally from FIG. 5, that there exists an essential difference between the two pulse waves, namely the distance e (demonstrating a time interval) signed at the pulse wave of the right brain hemisphere shows a length indicating a pathologic alternation (the internationally used limit value is 180 msec, which is highly surpassed by the value corresponding to the distance.

The invention is hereinafter described in detail by an Example.

EXAMPLE

The data of the patient examined (block 7 in FIG. 2) were as follows:

| name: | Y.X. |
|---|---|
| data of birth: | 18. 05. 1936, Budapest |
| body weight: | 79 kg |
| height: | 174 cm |
| time of the examination: | January 5, 1992 |
| sex of the patient: | woman. |

After taking up the above data, the following questions were posed to the person examined and answered negatively (block 8 in FIG. 2):

Do you smoke?

Do you systematically consume alcohol?

Do you suffer from high blood pressure?

Do you suffer from heart disease?

Do you suffer from diabetes?

Immediately after answering the questions, the first stress examination was carried out /block 9 in FIG. 2 (Table 1)/, within the framework of which a) the blood pressure and pulse frequency (heart rate) of the patient were measured. The result of measurement was as follows:

120/85; 74/minute b) questions were posed for determination of the temporary anxiety (brief variant of the Spielberger test) and the responses were recorded.

In the next step, our questions relating to the neurological symptoms indicating cerebral vascular spasm (TIA) were posed (block 10 in FIG. 2, i.e. the neurological block). These were targeted essentially to the following syndromes:

temporary weakness of extremities, numbness, sensory decrease;

temporary numbness, sensory disturbance on the face or trunk;

transitory disturbance of speaking, vision, swallowing dizziness, temporary apraxia of extremities and loss of consciousness;

loss of memory, transitory disturbance of reading, writing, counting or spatial orientation;

other disturbances considered to be of nervous system origin.

On the questionary cited above the questions can be summarized according to Table 2. The patient responded to the questions relating to the above syndromes in several cases in such a manner that he has disturbances on his left side (temporary weakness on the left foot, temporary numbness on the left foot, left face and left part of the trunk); feeling of uncertainty at the left, apraxia of the left extremities). In addition, he indicated disturbance of speaking and disturbances in the vision of both eyes.

The above questions and responses are fixed (recorded) by filling out the questionary several times mentioned previously. After filling out the questionary and after inscribing the informations obtained into a database treating program, they are charged to a computer (FIG. 1) including also the responses given to the first stress examination.

By answering and entering the above questions into a computer, the major part of verbal examination has been closed. Thereafter, the electrodes required to EEG and REG examinations were fastened to the patient seated, then she lay backwards onto the examinating bed. Then, the electrodes required for examining ECG and extremity pulses were placed onto her body (above the wrist and ankle both on the right and left sides). The electrodes join to signal receiver-transformer channels forming a part of the patient-inserting unit connected with the computer mentioned above (FIG. 1) namely, they are the inputs thereof. By starting the computer program, the measurement and data processing of the analogue physiological signals, namely EEG, REG and ECG signals are initiated (FIG. 3).

The following data were obtained as a result of this operation (process).

TABLE 4

| Measurement data of recordings | | |
|---|---|---|
| Left side | | Right side |
| 10.2/1.4.6 | dominant frequency of EEG [Hz]amplitude On the head, amplitude/time [msec] | 10.2/9.77 |
| −20.3/131 | 1st minimum | −11.7/140 |
| 30.5/368 | maximum | 17.7/362 |
| | On the neck, amplitude/time [msec] | |
| −11.7/149 | 1st min. | 3.91/419 |
| 61.7/476 | Max. | 66.4/707 |
| | On the arm, amplitude/time [msec] | |
| −16.4/179 | 1st min. | −16.4/176 |
| 9.37/254 | max. | 14.8/254 |
| | 2nd min. | −9.37/1656 |
| | On the foot, amplitude/time [msec] | |
| −7.03/−70 | 1st min. | −1.56/−70 |
| 26.6/53 | max. | 23.4/53 |

The graphical illustration of data of the first line (EEG frequency spectrum) was also carried out (FIG. 4). Similarly, the REG displayed in the 2nd line (pulse wave on the head) was graphically demonstrated. However, the graphical illustration is not indispensably required; at most in the case when it can be perceived in this phase of examination that further examination of circulation will be performed.

Immediately after disassembling the electrodes, the second stress examination (block 12 in FIG. 2, Table 1) was carried out, within the framework of which the blood pressure and pulse frequency (heart rate) were again measured and gave the following results:

130/80 and 60/minute and responses were asked to the same questions as in the first stress examination; these responses as a continuation of the former (previous) database were also entered into the computer.

From the results of examination recorded by the computer, the findings were formed namely, the following decision was made.

a) Based on the questionary, the following status can be concluded, which can be judged to be pathologic:

based on the symptoms of the left side, the circulation disturbance of the right brain hemisphere can be supposed. No other sign indicating any pathological alteration was found. No response given to other questions (remaining as empty in the questionary) (other symptoms, block 16, FIG. 2) indicated that any disorder of circulation could be supposed in addition to that defined above.

b) Subsequently, the results of physiological data processing were evaluated, according to which:

no evaluable or pathological, respectively difference between the right and left sides (FIG. 4) exists in EEG and pulse waves of the extremities (blocks 18 and 20 as well as 24 in FIG. 3);

in the REG, also graphically represented in FIG. 5, a difference appears between the right and left brain hemispheres namely, the right-side pulse wave represents a pathological alteration indicating arteriosclerosis.

Based on these examinations of two kinds, our decision, i.e. the part "Opinion" of the findings (block 13 in FIG. 2) was as follows.

Check-up is suggested because of suspicion of disturbance in the brain circulation (blocks 14 and 15 in FIG. 2).

In relation to the Example it should be noted that the district physician would not have posed the groups of questions posed by us (namely, those are substantially neurological-professional asks), when the patient had turned to him and, on the other hand, he would have considered the complaints to be of psychic origin. However, if this physician had made to carry out the Doppler control on the patient, he would have obtained a negative result. It is noted that 28 persons belonging to our own patients were controlled by using the Doppler test and the result was in each case negative. Subsequently, the same group of patients were examined by using the process according to the invention and on about 80% (22 persons) of them, quantifiable differences were found in the pulse waves of head, hands and feet. Based on this, further examination of the affected persons was proposed, but at least a medical observation was suggested.

The advantageous effects connected with the invention may be summarized as follows.

The greatest advantage of the invention is that it provides to recognize in the possibly earliest phase the arteriosclerosis and preceding circulation disturbances (decrease in the wind box function of the vessel wall), which cannot yet be considered to be pathologic. By using the process according to the invention, the difference from the normal status can already be detected when an actual sclerosis of the vessel wall has not yet developed but its elasticity has been diminished; thus, the invention is an ideal tool for the prevention. (No process is known at present, which could be useful to early recognize the alterations (sclerosis of the vascular system; e.g. by using the Doppler method considered to be most up-to-date, the consequence of a sclerotic vessel wall inducing flow disturbance can only be measured). The process has (involves) no invasive element, it is patient-saving, pain-free and can be carried out during 30 minutes. It is considerably economic.

The process is equally useful both for screening examinations and performing tasks of patient-care. At the end of examination the participant receives the examination protocol containing the results and, when required, he can utilize it for further examinations.

The invention is of course not limited to the solvings described above but it can be accomplished in a number of ways within the scope of protection defined in the claims.

We claim:

1. A computer implemented method of diagnosing a circulation disorder of a patient, comprising the steps of:

recording, in a computer, whether the patient has experienced neurological disorder symptoms based on the patient's responses to questions;

sensing the patient's electrical brain activity;

recording the sensed electrical brain activity in the computer;

sensing the patient's rheographic pulse waves of at least one of the patient's head and a limb;

recording the sensed rheographic pulse waves in the computer;

processing the recorded information regarding whether the patient has experienced neurological disorder symptoms, the recorded electrical brain activity and the recorded rheographic pulse waves to determine whether the patient has a circulation disorder; and outputting a report indicative of whether the patient has a circulation disorder.

2. The method of claim 1, wherein the step of sensing the patient's electrical brain activity includes separately sensing the electrical brain activity of the right and left sides of the patient's brain and wherein the step of recording the sensed electrical brain activity includes separately recording the sensed electrical brain activity of the right and left sides of the patient's brain.

3. The method of claim 1, wherein when the step of sensing the patient's rheographic pulse waves comprises sensing the rheographic pulse waves of the patient's head, the step comprises separately sensing the rheographic pulse waves of the right and left sides of the patient's head, wherein when the step of sensing the patient's rheographic pulse waves comprises sensing the rheographic pulse waves of a limb, the step comprises separately sensing the rheographic pulse waves of corresponding right and left limbs, and wherein the step of recording the sensed rheographic pulse waves comprises separately recording the sensed rheographic pulse waves from the patient's right and left sides.

4. The method of claim 1, further comprising the steps of:

sensing the patient's electrical heart activity; and recording the sensed electrical heart activity in the computer, and wherein the processing step further includes processing the recorded electrical heart activity.

5. The method of claim 4, wherein the step of sensing the patient's electrical brain activity includes separately sensing the electrical brain activity of left and right sides of the patient's brain, wherein the step of recording the sensed electrical brain activity includes separately recording the sensed electrical brain activity of left and right sides of the patient's brain, wherein the step of sensing the patient's rheographic pulse waves comprises separately sensing the rheographic pulse waves at the left and right sides of the patient's head, and wherein the step of recording the sensed rheographic pulse waves comprises separately recording the sensed rheographic pulse waves from the right and left sides of the patient's head.

6. The method of claim 5, wherein the step of sensing the patient's rheographic pulse waves comprises separately sensing the rheographic pulse waves at left and right sides of the patient's head and separately sensing the pulse waves of corresponding right and left limbs of the patient, and wherein the step of recording the sensed rheographic pulse waves comprises separately recording the sensed pulse waves of the right and left sides of the patient's head and the corresponding right and left limbs of the patient.

7. The method of claim 1, further comprising the steps of:
performing a stress test; and
recording the results of the stress test in the computer, and wherein the processing step includes processing the recorded results of the stress test.

8. The method of claim 7, wherein the step of performing a stress test comprises the steps of:
sensing the patient's blood pressure;
sensing the patient's pulse rate; and
assessing the patient's anxiety level based on the patient's responses to questions; and
wherein the step of recording the results of the stress test comprises recording the sensed blood pressure and pulse rate and recording the patient's responses to questions designed to reveal the patient's anxiety level.

9. The method of claim 7, wherein the step of performing a stress test comprises performing a first stress test before performing the steps of sensing the patient's electrical brain activity and sensing the patient's rheographic pulse waves, wherein the method further comprises the steps of:
performing a second stress test after the patient's electrical brain activity and rheographic pulse waves have been sensed; and
recording the results of the second stress test in the computer, and wherein the processing step includes processing the recorded results of the first and second stress tests.

10. The method of claim 1, further comprising the step of recording, in the computer, whether the patient exhibits at least one arteriosclerosis risk factor based on the patient's responses to questions, and wherein the processing step includes processing the recorded information regarding whether the patient exhibits at least one arteriosclerosis risk factor.

11. The method of claim 1, further comprising the step of recording, in the computer, patient physical data, wherein the patient physical data includes at least one member selected from the group consisting of the patient's age, weight, height, sex, blood cholesterol level and blood sugar level, and wherein the processing step includes processing the recorded patient physical data.

12. An apparatus for diagnosing a circulation disorder of a patient, comprising:
means for recording, in a computer, whether the patient has experienced neurological disorder symptoms based on the patient's responses to questions;

means for recording the patient's electrical brain activity;

means for recording the patient's rheographic pulse waves of at least one of the patient's head and a limb;

means for processing the recorded information regarding whether the patient has experienced neurological disorder symptoms, the recorded electrical brain activity and the recorded rheographic pulse waves to determine whether the patient has a circulation disorder; and means for outputting a report indicative of whether the patient has a circulation disorder.

13. The apparatus of claim 12, wherein the means for recording the patient's electrical brain activity includes means for separately recording the electrical brain activity of the right and left sides of the patient's brain.

14. The apparatus of claim 12, wherein the means for recording the patient's rheographic pulse waves comprises means for separately recording the rheographic pulse waves from the patient's right and left sides.

15. The apparatus of claim 12, further comprising means for recording the patient's electrical heart activity, wherein the processing means includes means for processing the recorded electrical heart activity.

16. The apparatus of claim 15, wherein the means for recording the patient's electrical brain activity includes means for separately recording the electrical brain activity of the right and left sides of the patient's brain, and wherein the means for recording the patient's rheographic pulse waves comprises means for separately recording rheographic pulse waves from the patient's right and left sides.

17. The apparatus of claim 12, further comprising:
means for recording the patient's blood pressure;
means for recording the patient's pulse rate; and
means for recording the patient's anxiety level based on the patient's responses to questions designed to reveal the patient's anxiety level, wherein the processing means includes means for processing the recorded blood pressure, pulse rate and patient anxiety level.

18. The apparatus of claim 12, further comprising means for recording whether the patient exhibits at least one arteriosclerosis risk factor based on the patient's responses to questions, and wherein the processing means includes means for processing the recorded information regarding whether the patient exhibits at least one arteriosclerosis risk factor.

19. The apparatus of claim 12, further comprising means for recording patient physical data, wherein the patient physical data includes at least one member selected from the group consisting of the patient's age, weight, height, sex, blood cholesterol level and blood sugar level, and wherein the processing means includes means for processing the recorded patient physical data.

20. An apparatus for diagnosing a circulation disorder of a patient, comprising:
at least one memory device for recording whether the patient has experienced neurological disorder symptoms based on the patient's responses to questions, for recording the patient's electrical brain activity and for recording the patient's rheographic pulse waves of at least one of the patient's head and a limb;

a processor programmed to provide a report indicative of whether the patient has a circulation disorder based on the recorded information regarding whether the patient has experienced neurological disorder symptoms, the recorded electrical brain activity and the recorded rheographic pulse waves; and an output device for outputting said report.

21. The apparatus of claim 20, wherein the processor separately processes recorded electrical brain activity of the right and left sides of the patient's brain.

22. The apparatus of claim 20, wherein the processor separately processes recorded rheographic pulse waves from the patient's right and left sides.

23. The apparatus of claim 20, wherein said at least one memory device also records the patient's electrical heart activity, and wherein the processor is programmed to provide a report indicative of whether the patient has a circulation disorder based, in part, on the recorded electrical heart activity.

24. The apparatus of claim 20, wherein said at least one memory device records the patient's blood pressure, pulse rate and the patient's responses to questions designed to reveal the patient's anxiety level, and wherein the processor is programmed to provide a report indicative of whether the patient has a circulation disorder based, in part, on the recorded blood pressure and pulse rate and the recorded patient responses to questions designed to reveal the patient's anxiety level.

25. The apparatus of claim 20, wherein said at least one memory device records whether the patient exhibits at least one arteriosclerosis risk factor based on the patient's responses to questions, and wherein the processor is programmed to provide a report indicative of whether the patient has a circulation disorder based, in part, on the recorded information regarding whether the patient exhibits at least one arteriosclerosis risk factor.

26. The apparatus of claim 20, wherein the at least one memory device records at least one item of patient physical data selected from the group consisting of the patient's age, weight, height, sex, blood cholesterol level and blood sugar level, and wherein the processor is programmed to provide a report indicative of whether the patient has a circulation disorder based, in part, on the recorded patient physical data.

* * * * *